US012636467B2

(12) United States Patent
Wang et al.

(10) Patent No.: US 12,636,467 B2
(45) Date of Patent: May 26, 2026

(54) CATHETER CLAMPING DEVICE

(71) Applicant: enableCV, LLC, Midvale, UT (US)

(72) Inventors: John X. Wang, Orange, CA (US);
Bryan A. Janish, Huntington Beach,
CA (US); Zoey Cancilla Than, La
Habra Heights, CA (US); **Thaddeus
Lee Young, Chino, CA (US); Kemani
Kwame Rodgers**, Lockport, NY (US);
Lawrence Luan Tran, Huntington
Beach, CA (US); **Ashley Krystin
Barks**, Foothill Ranch, CA (US)

(73) Assignee: enableCV, LLC, Midvale, UT (US)

( * ) Notice: Subject to any disclaimer, the term of this
patent is extended or adjusted under 35
U.S.C. 154(b) by 1054 days.

(21) Appl. No.: 17/650,239

(22) Filed: Feb. 7, 2022

(65) Prior Publication Data

US 2022/0161002 A1 May 26, 2022

Related U.S. Application Data

(63) Continuation of application No. PCT/US2020/
044207, filed on Jul. 30, 2020.

(60) Provisional application No. 62/885,141, filed on Aug.
9, 2019.

(51) Int. Cl.
| | |
|---|---|
| *A61M 25/02* | (2006.01) |
| *A61B 1/00* | (2006.01) |
| *A61M 39/28* | (2006.01) |
| *A61M 39/06* | (2006.01) |

(52) U.S. Cl.
CPC ......... *A61M 25/02* (2013.01); *A61B 1/00148*
(2022.02); *A61M 39/28* (2013.01);
(Continued)

(58) Field of Classification Search
CPC .................. A61M 25/02; A61M 39/28; A61M
2025/024; A61M 2039/062;
(Continued)

(56) References Cited

U.S. PATENT DOCUMENTS

| | | | | |
|---|---|---|---|---|
| 4,842,592 | A | * | 6/1989 | Caggiani ............... A61M 39/12 |
| | | | | 285/334.2 |
| 5,161,428 | A | | 11/1992 | Petruccello |
| | | | | (Continued) |

FOREIGN PATENT DOCUMENTS

WO     2013118807 A1     8/2013

OTHER PUBLICATIONS

European Search Report, as issued in connection with European
Application No. 25213122.2, dated Jan. 28, 2026, 11 pgs.

*Primary Examiner* — Laura A Bouchelle
*Assistant Examiner* — Marissa Taylor
(74) *Attorney, Agent, or Firm* — Maschoff Brennan; Paul
G. Johnson

(57) ABSTRACT

A clamping device for a shaft of a catheter can include a first
member rotatably coupled to a second member. The first
member can have an annular element defining a central
lumen, the outer surface of the annular element having a
non-circular cross-sectional profile, and the second member
can define a bore into which the annular element extends, the
bore having a non-circular cross-sectional profile. The
device can move between a release state wherein the central
lumen has a first diameter, and a clamped state wherein the
central lumen has a second diameter less than the first
diameter. When the clamping device is in the clamped state,
the clamping device can engage an outer surface of a
catheter shaft and when the clamping device is in the release
state, the clamping device can be moved along a length of
the catheter shaft.

15 Claims, 10 Drawing Sheets

(52) U.S. Cl.
CPC . *A61M 2025/024* (2013.01); *A61M 2039/062* (2013.01); *A61M 2039/0673* (2013.01); *A61M 2210/127* (2013.01)

(58) Field of Classification Search
CPC .... A61M 2039/0673; A61M 2210/127; A61B 1/00148; F16L 3/08; F16L 3/1041; F16B 2/02
See application file for complete search history.

(56)                References Cited

U.S. PATENT DOCUMENTS

| | | | |
|---|---|---|---|
| 5,279,597 A * | 1/1994 | Dassa | A61M 25/0111 604/165.04 |
| 5,394,770 A | 3/1995 | Boike et al. | |
| 6,547,760 B1 | 4/2003 | Samson et al. | |
| 6,908,454 B2 | 6/2005 | McFarlane | |
| 7,175,184 B1 | 2/2007 | Rinner et al. | |
| 7,316,669 B2 | 1/2008 | Ranalletta | |
| 9,149,606 B2 | 10/2015 | Beissel et al. | |
| 9,326,784 B2 | 5/2016 | Ravikumar | |
| 9,636,105 B2 | 5/2017 | Bagaoisan et al. | |
| 2013/0030519 A1 | 1/2013 | Tran et al. | |
| 2013/0184742 A1 | 7/2013 | Ganesan et al. | |
| 2013/0281979 A1* | 10/2013 | Arnim | A61M 25/0147 604/509 |
| 2014/0336584 A1 | 11/2014 | McFarlane | |
| 2015/0051584 A1 | 2/2015 | Korkuch et al. | |
| 2015/0123355 A1 | 5/2015 | Castro et al. | |
| 2015/0148747 A1 | 5/2015 | Whitley | |

* cited by examiner 411
416
400
412
404
402
408
403
418
413
414

412
411
400
416
402
403
404
456
418
413
414

CATHETER CLAMPING DEVICE

CROSS REFERENCE TO RELATED APPLICATIONS

This application is a continuation of International Application No. PCT/US2020/044207, filed Jul. 30, 2020, which claims the benefit of U.S. patent application Ser. No. 62/885,141 filed Aug. 9, 2019, the entire disclosures all of which are incorporated by reference for all purposes.

FIELD

This disclosure relates generally to clamping devices and methods for clamping catheter assemblies.

BACKGROUND

Catheter assemblies can be used for a variety of interventional procedures including aortic occlusion, angioplasty, urinary catheterization, nephrostomy, hemodialysis, medical device implantation, etc. In many procedures a distal end portion of the catheter assembly is positioned at a selected site within the body and maintained at that site for a selected time or throughout the duration of the procedure.

Methods and devices have been developed for mitigating or preventing movement of the distal end portion of the catheter assembly away from the selected site. However, such devices can be unwieldly or difficult for a physician to actuate during a catheterization procedure. Accordingly, a need exists for improved devices and methods for mitigating or preventing movement of a catheter assembly.

SUMMARY

Described herein are examples of a clamping device for use with a catheter assembly, as well as methods for using the same. The clamping device can be used to secure a catheter against movement relative to one or more other objects, including introducer assemblies, or other catheters.

In a representative example, a clamping device for a shaft of a catheter can comprise a first member and a second member rotatably coupled to the first member. The first member can comprise an annular element defining a central lumen, the annular element having an outer surface having a non-circular cross-sectional profile. The second member can define a bore into which the annular element extends, the bore having a non-circular cross-sectional profile. The clamping device can be movable between a first, release state in which the second member is in a first rotational position relative to the first member and the central lumen has a first diameter, and a second, clamped state in which the second member is in a second rotational position relative to the first member and the central lumen has a second diameter, which is less than the first diameter. When the clamping device is in the clamped state, the clamping device can engage an outer surface of a catheter shaft extending through the central lumen and when the clamping device is in the release state, the clamping device can be moved along a length of the catheter shaft.

In some examples, the clamping device further comprises an elastomeric member disposed within the central lumen of the first member, the elastomeric member defining a second lumen sized to receive the catheter shaft.

In some examples, the annular element can comprise one or more engagement members extending longitudinally along the annular element and defining a non-circular outer profile of the annular element. In some examples, the engagement members can comprise chamfered rectangular protrusions.

In some examples, when in the clamped state, the bore and the annular element are rotationally offset from one another such that the annular element is compressed by the bore, thereby reducing the diameter of the central lumen. In some examples, when the bore and the annular element are rotationally offset from one another, the engagement members are deflected inwardly toward the central lumen.

In some examples, when in the release state, the bore and the annular element are rotationally aligned with one another.

In some examples, the bore of the second member comprises a lip portion configured to engage one or more end surfaces of the one or more engagement members such that the first and second members form a snap-fit connection.

In some examples, the annular element comprises one or more openings extending longitudinally along the annular element and spaced apart about a circumference of the annular element. In some examples, when the clamping device is in the release state the openings have a first width and when the clamping device is in the clamped state the openings have a second width narrower than the first width.

In some examples, the clamping device can further comprise a first pair of extension members and a second pair of extension members, wherein when the first pair of extension members abut each other the clamping device is in the release state and when the second pair of extension members abut each other the clamping device is in the clamped state. In some examples, the second pair of extension members comprise indicia configured to indicate to a user that the clamping device is in the clamped state. In some examples, the indicia can be tactile indicia.

In a representative example, a catheter assembly can comprise a shaft and a clamping device. The clamping device can be disposed on the shaft and can include a first member defining a central lumen and a second member rotatably coupled to the first member, the first and second members being fixed axially relative to one another. The clamping device can be movable between a first, release state wherein the central lumen has a first diameter and the clamping device can be moved along a length of the catheter shaft and a second, clamped state wherein the central lumen has a second diameter smaller than the first diameter and the clamping device can engage an outer surface of the shaft extending through the central lumen.

In some examples, the first member comprises an annular element having a non-circular cross-section and the second member comprises a bore into which the annular element extends, the bore having a non-circular cross section. In some examples, when in the release state, the non-circular cross-section of the annular element is rotationally aligned with the non-circular cross-section of the bore, and wherein when in the clamped state the non-circular cross-section of the annular element is rotationally offset from the non-circular cross-section of the bore.

In some examples, the assembly further comprises a tubular elastomeric member disposed within the clamping device such that the shaft extends through a lumen of the elastomeric member. In some examples, when in the clamped state, an inner surface of the elastomeric member frictionally engages the outer surface of the shaft.

A representative method can comprise moving a clamping device in a release state along a length of a shaft of a medical device to a selected clamping site. The clamping device can comprise a first member rotatable coupled to a second member, the first and second members being fixed axially relative to one another. The method can further comprise clamping the clamping device at the selected clamping site along the length of the shaft by rotating the first and second members relative to one another to move the clamping device from the release state to the clamped state.

In some examples, the method can further comprise abutting the clamping device in the clamped state against a proximal end of another medical device through the shaft extends to prevent movement of the shaft relative to another medical device in one direction.

In some examples, the first member comprises an annular element having a non-circular cross-section and the second member comprises a bore having a non-circular cross-section and wherein rotating the first and second members relative to one another moves the annular element and the bore between a rotationally aligned configuration and a rotationally offset configuration.

In some examples, the first member comprises an annular element having a first bore, an outer surface of the annular element having a non-circular shape in cross-section, and the second member comprises a body portion including a second bore having a non-circular shape in cross-section into which the annular element extends, and wherein when in the clamped state, the second bore and the annular element are rotationally offset from one another such that the annular element is compressed by the second bore, thereby reducing the diameter of the first bore.

Any method for performing a medical procedure on a patient disclosed herein can also be used for simulating a medical procedure on a simulated patient or anatomic ghost, which is useful, for example, for training, teaching, demonstration, and the like. The simulated patient can be a simulated human or non-human patient, and can include physical, virtual, or both physical or virtual components; and can simulate a whole body, or a portion or portions thereof, for example, a heart, or a heart and a portion of a circulatory system. All or a portion of the simulated patient can have a biological origin, for example, from a human or animal cadaver; can be artificial or man-made; or have any combination of biological and artificial components.

A representative example provides a clamping device for a shaft of a catheter comprising a first member and a second member rotatably coupled to the first member. The first member can comprise an annular element having a first bore, with an outer surface of the annular element having a non-circular shape in cross-section formed by one or more engagement members extending from the outer surface of the annular element. The second member can comprise a body portion including a second bore having a non-circular shape in cross-section into which the annular element extends. Rotating the first and second members relative to one another can move the clamping device between a first state in which the first bore has a first diameter and a second state wherein the first bore has a second diameter smaller than the first diameter. When the clamping device is in the second state, the clamping device can be configured to engage an outer surface of a catheter shaft extending through the central lumen and when the clamping device is in the release state, the clamping device can be configured such that it can move along a length of the catheter shaft.

In some examples, the first and second members are fixed axially relative to one another.

In some examples, the engagement members comprise chamfered rectangular protrusions extending longitudinally along at least a portion of the annular element.

In some examples, when in the second state, the second bore and the annular element are rotationally offset from one another such that the annular element is compressed by the second bore, thereby reducing the diameter of the first bore. In some examples, when the second bore and the annular element are rotationally offset from one another, the engagement members are deflected inwardly toward the central lumen.

In some examples, when in the release state, the second bore and the annular element are rotationally aligned with one another.

Some examples further comprise an elastomeric member disposed within the first bore of the first member, the elastomeric member defining an additional bore sized to receive the catheter shaft.

In some examples, the second bore comprises a lip portion configured to engage one or more end surfaces of the one or more engagement members such that the first and second members form a snap-fit connection.

In some examples, the annular element comprises one or more openings, the openings extending radially through a wall of the annular element. In some examples, the opening extends longitudinally along an annular element and are spaced apart about a circumference of the annular element. In some examples, when the clamping device is in the release state the openings have a first width and when the clamping device is in the clamped state the openings have a second width narrower than the first width.

Some examples further comprise a first pair of extension members extending radially outward from the first member and a second pair of extension members extending radially outward from the second member, wherein when a first extension member of the first pair of extension members abuts a first extension member of the second pair of extension members the clamping device is in the release state and when a second extension member of the first pair of extension members abuts a second extension member of the second pair of extension members the clamping device is in the clamped state. In some examples, the second extension member of each pair of extension members comprises indicia configured to indicate to a user that the clamping device is in the clamped state. In some examples, the indicia are tactile indicia. In some examples, the indicia are cutouts in an edge portion of each second extension member.

A representative example provides clamping device for a shaft of a catheter, comprising a first member and a second member axially fixed relative to the first member. The first member can include an annular element having a central bore, an outer surface of the annular element having a non-circular outer profile in cross-section. The second member can include a body portion including an opening having a non-circular shape in cross-section into which the annular element extends. The first and second members can be rotatable relative to one another between a rotationally aligned position wherein the central bore has a first diameter and a rotationally offset position wherein the opening compresses the central bore of the annular element to a second diameter smaller than the first diameter.

In some examples, the annular element comprises one or more engagement members extending longitudinally along the annular element and defining the non-circular outer profile of the annular element.

In some examples, the first member comprises first and second extension portions extending radially from the first member in opposing directions, and wherein the second member comprises third and fourth extension members extending radially from the second member in opposing directions. In some examples, movement of the first extension portion and the third extension portion toward one another rotates the first member relative to the second member to a first position wherein the first bore has a first diameter. In some examples, movement of the second extension portion and the fourth extension portion toward one another rotates the first member relative to the second member to a second position wherein the second bore compresses the annular element such that the first bore has a second diameter smaller than the first diameter such that the clamping device is in a clamped state. In some examples, the second and fourth extension portions comprise tactile indicia. In some examples, the tactile indicia are cutouts in respective edge portions of the second and fourth extension portions.

A representative example provides a clamping device for a shaft of a catheter, comprising a first member and a second member axially fixed relative to the first member. The first member can include an annular element having a first bore, a first extension portion, and a second extension portion, an outer profile of the annular element having a non-circular shape in cross-section. The second member can include a body portion including a third extension portion, a fourth extension portion, and a second bore having a non-circular shape in cross-section into which the annular element extends. Movement of the first extension portion and the third extension portion toward one another can rotate the first member relative to the second member to a first position wherein the first bore has a first diameter. Movement of the second extension portion and the fourth extension portion toward one another can rotate the first member relative to the second member to a second position wherein the second bore compresses the annular element such that the first bore has a second diameter smaller than the first diameter.

Some examples further comprise an elastomeric member disposed within the first bore, the elastomeric member defining a third bore sized to receive a catheter shaft.

In some examples, the annular element comprises one or more engagement members extending longitudinally along the annular element and defining a non-circular outer profile of the annular element. In some examples, the engagement members comprise chamfered rectangular protrusions. In some examples, when the second bore and the annular element are rotationally offset from one another, the engagement members are deflected inwardly toward the central lumen.

In some examples, the second bore a lip portion configured to engage one or more end surfaces of the one or more engagement members such that the first and second members form a snap-fit connection.

In some examples, the annular element comprises one or more openings extending longitudinally along the annular element and spaced apart about a circumference of the annular element. In some examples, when the clamping device is in the release state the openings have a first width and when the clamping device is in the clamped state the openings have a second width narrower than the first width.

The foregoing and other objects, features, and advantages will become more apparent from the following detailed description, which proceeds with reference to the accompanying figures.

DETAILED DESCRIPTION

Described herein are examples of a catheter clamping device for use with a catheter assembly. Though some of the below examples are described with respect to an antegrade cardioplegia delivery catheter, the clamping device can be used with any catheter assembly.

Figure 1:
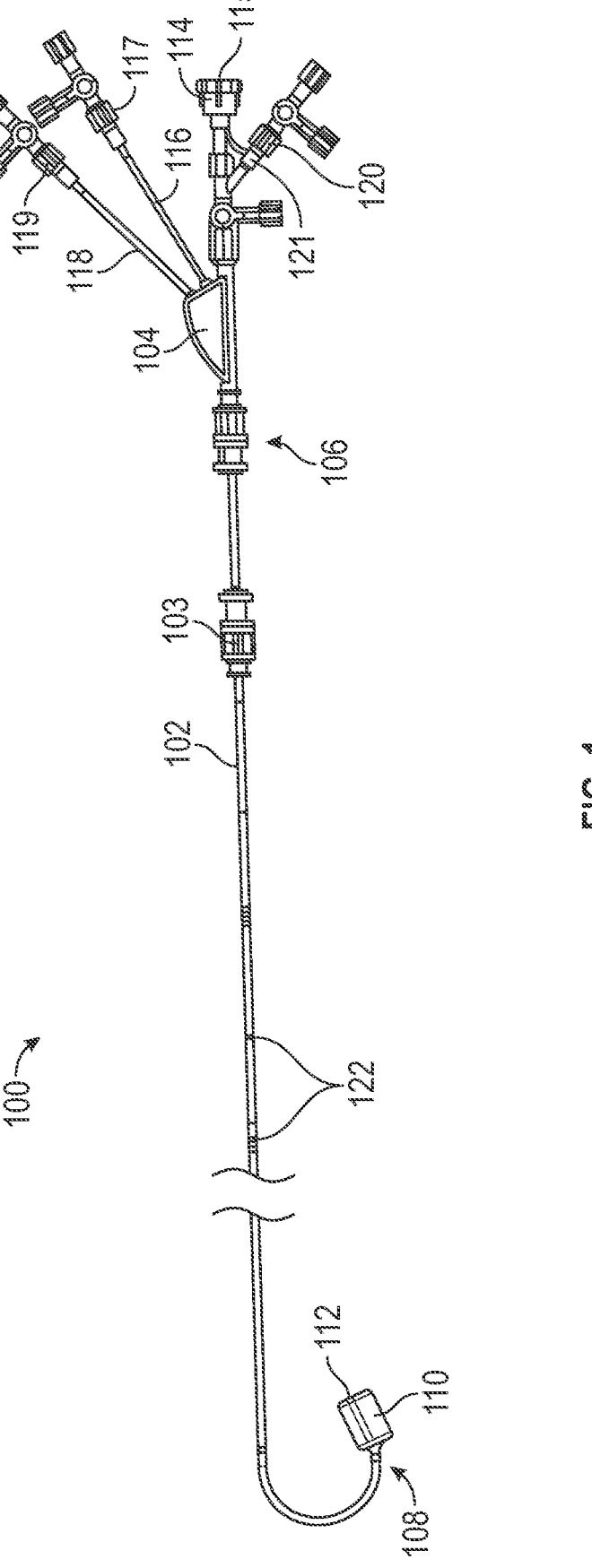
FIG. 1 is a side view of an exemplary catheter assembly configured as an antegrade cardioplegia delivery catheter.

An exemplary example of a catheter assembly configured as an antegrade cardioplegia delivery catheter 100 is illustrated in FIG. 1. A distal end of the delivery catheter 100 can be inserted into a patient using, for example, an introducer assembly (see e.g., FIG. 10) comprising an introducer cannula and a hemostasis valve. The hemostasis valve can be configured to allow passage of the delivery catheter 100 therethrough.

As shown in FIG. 1, in the illustrated example, the delivery catheter 100 includes a catheter shaft 102 that can be inserted into a patient and located at a desired location, such as within the ascending aorta of the patient. Accordingly, the shaft 102 may have a length such that when a distal end 108 of the shaft 102, including an expandable member 110, is at a desired location within the patient, a proximal end 106 of the shaft 102 may remain exterior to the patient. The proximal end 106 of the shaft 102 may be positioned, for instance, adjacent a peripheral access site, such as in the femoral artery to facilitate a minimally invasive procedure. A hub 104 may also be attached to the shaft 102. The hub 104 may serve any number of purposes. For instance, in the example shown in FIG. 1, the hub 104 may have various extension arms 114, 116, 118, 120 that serve various purposes. Such extension arms may, for instance, facilitate expansion of the expandable member 110, delivery of cardioplegic fluid, monitoring of pressure or characteristics within the vasculature at the distal tip 112, insertion of guidewires, stents, replacement valves, other devices or components, or any combination of the foregoing. Extension arm 114 can comprise a rotating hemostasis valve, which can be connected to the central lumen of catheter shaft 102 to allow for guidewire insertion, fluid injection (e.g., cardioplegia delivery), and aortic root venting.

The delivery catheter 100 can also include a clamping device 103 disposed on the shaft 102 that can be used to retain the distal end 108 of the shaft 102 including the expandable member no at a selected position within the body of a patient, as described in more detail below.

The delivery catheter 100 may be used to occlude a portion of a patient's vasculature at or near the heart, while also supplying cardioplegic fluid to the heart. An exemplary manner in which the delivery catheter 100 can be used to occlude vasculature may be understood particularly with reference to FIGS. 2-4.

The delivery catheter 100 may include an expandable member no. The expandable member 110 may be generally positioned at the distal end 108 of the shaft 102, and may be proximate or adjacent a distal tip 112 of the shaft 102. The expandable member no may be configured to vary its size, diameter, or other dimension in any suitable manner. In some examples, the expandable member no is an expandable balloon. By way of illustration, the expandable member no may be formed of a flexible material. The expandable member no may, for instance, be polyurethane, PTFE, or other material that is blow-molded, dip-molded, or otherwise formed. The expandable member no may also be formed of other materials, formed in other manners, or take other forms. For instance, the expandable member no need not be a balloon, and could be any other suitable type of selectively expandable element.

Figures 2, 3, 4:
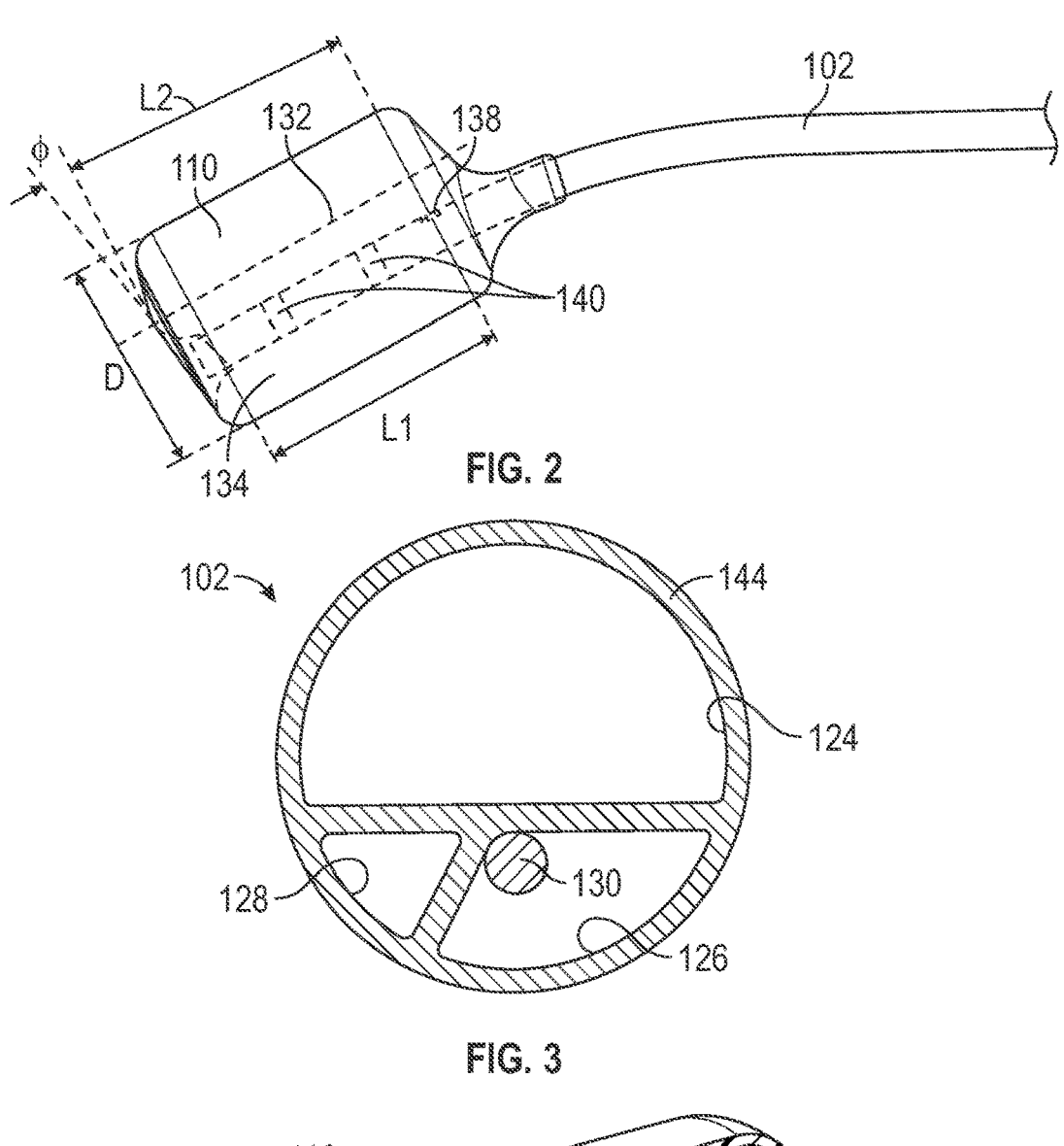
FIG. 2 is a side view of the distal end of the delivery catheter of FIG. 1.
FIG. 3 is a cross-sectional view of a shaft of the delivery catheter of FIG. 1.
FIG. 4 is a perspective cross-sectional view of an atraumatic tip of the delivery catheter of FIG. 1.

The expandable member no of FIGS. 2 and 4 is illustrated in an expanded state. It should be appreciated, however, that the expandable member no may be inserted into a patient while in a collapsed, partially collapsed, or other state that may allow the expandable member no to pass more easily through the patient's vasculature. In some examples, as the expandable member no moves through the vasculature, the expandable member no does not substantially occlude the vasculature, at least not until the distal tip 112 of the shaft 102 is at or near an intended location. Once at the desired location, the expandable member no may be expanded.

Expansion of the expandable member 110 may be performed in any suitable manner. For instance, where the expandable member no is an expandable balloon, a fluid may be selectively passed through the shaft 102 and into the expandable member no. In FIG. 1, for instance, the shaft 102 may connect to the hub 104, and may be in fluid communication with one or more of the various extension arms 114, 116, 118, 120. The shaft 102 may have one or more lumens therein to receive fluid, instruments, or other items. For instance, as shown in FIGS. 3 and 4, the shaft 102 may have a multi-lumen design. Each of the multiple lumens 124, 126, 128 may be in communication with the one or more extension arms 114, 116, 118, 120 (FIG. 1) with access ports 115, 117, 119, 121, which may act as access ports to the respective lumens 124, 126, 128.

In the illustrated example, the shaft 102 may include a primary lumen 124 and multiple secondary lumens 126, 128. The secondary lumen 126 may, for instance, extend along a length of the shaft 102 and terminate at a location within the expandable member no. As shown in FIG. 4, for instance, the secondary lumen 126 may terminate near the distal tip 112 of the shaft 102. The secondary lumen 126 may be in fluid communication with an inflation port 138 that extends through a sidewall of the shaft 102. The inflation port 138 can be within the expandable member 110, such that as fluid is inserted through the lumen 126 and exits the shaft 102 through the inflation port 138, the expandable member no may inflate or otherwise expand. Conversely, fluid dispelled from the expandable member 110 may pass through the inflation port 138 and into the shaft 102 as the expandable member 110 contracts.

The expandable member no may have any number of suitable constructions or configurations. For instance, in FIG. 4, the expandable member 110 is illustrated as an inflated balloon having a generally elongated, hexagonal side profile, and with the shaft 102 being eccentric relative to the central axis 132 of the expandable member no. The particular dimensions and configuration of the expandable member 110 can vary as desired to, for example, occlude an ascending aorta of a patient. In some examples, the dimension D corresponds to a diameter or width of the expandable member 110 and can generally correspond to the width of the ascending aorta at a desired occlusion location. For instance, the ascending aorta in an average adult may measure between about 3-5 and about 3.8 cm. Accordingly, in some examples, the expanded diameter D is about 3 cm to about 4 cm. The working length $L_1$ may also correspond to a length of the expandable member no that can engage the lower surface of the aorta to facilitate occlusion. In general, an increased working length $L_1$ increases the surface area for contact with the aorta and favors stabilizing the position of the expandable.

The expandable member 110 may generally be considered has being divided by the shaft 102 into a lower portion 134 and an upper portion 136. In this example, the upper and lower portions 134, 136 have different lengths L1, L2. The eccentric profile of the shaft 102 may provide differing sizes of portions 134, 136; however, the general shape of the expandable member 110 may additionally or alternatively be varied. In this example, for instance, the upper portion 136 may have a side surface extending at an angle φ from the distal tip 112, and to an upper contact surface, such that the length of the upper contact surface has the length L2. The length L2 may be greater or smaller than the working length L1. In the illustrated example, for instance, the angle φ may be between about ten and about twenty-five degrees, and more particularly between about thirteen and about twenty-one degrees. For instance, the angle φ may be between about fifteen and about eighteen degrees, such that the length L1 is greater than the length L2.

The expandable member no is but one example of a suitable expandable member, and other expandable members may be used. For instance, in other examples, the expandable member no may be spherical, trapezoidal, cylindrical, barrel-shaped, or otherwise configured. Moreover, the degree of eccentricity of the shaft 102 relative to the central axis 132 may also be varied. For instance, the shaft 102 may be concentric with the axis 132 (e.g., 0% eccentricity) or may vary up to nearly 100% eccentricity (e.g., the shaft at the upper or lower surface of the expandable member). In one example, the eccentricity of the shaft 102 may be between about 5% and about 36%.

To facilitate cardioplegic functions of the delivery catheter 100, the delivery catheter 100 may allow cardioplegic fluid to be passed from a fluid source or reservoir and into the ascending aorta or other location within a patient. FIGS.

3 and 4 illustrate a particular manner in which such features can be provided. For instance, as noted previously, the shaft 102 optionally includes multiple fluid conduits, channels, lumens, or other features. In particular, in the illustrated example, the shaft 102 may include a primary lumen 124 that is optionally in fluid communication with an extension arm 114 that acts as a port to allow the introduction of cardioplegic fluid, guidewires, surgical instruments, or other elements. Cardioplegic fluid may be pressurized and passed through the lumen 124 towards the distal tip 112 of the shaft 102. As best shown in FIG. 4, the distal end of the shaft 102 may include an opening generally corresponding to the lumen 124. For instance, the lumen 124 may be open at the distal tip 112 such that the pressurized cardioplegic fluid exits the shaft 102 distal to the expandable member 110.

In some examples, the distal tip 112 may be integrally formed with the shaft 102, although in other examples the distal tip 112 and shaft 102 are separate components that are bonded together. For instance, the distal tip 112 may be a molded, extruded, or otherwise formed component that is bonded to the shaft 102 using a thermal bonding, adhesive, laser welding, overmolding, or other procedure. In some examples, the expandable member may extend at least slightly distal relative to the distal tip. In such an example, the lumens at the distal tip may be protected by the expandable member. For instance, a distal leg of the expandable member may connect to the distal tip of the shaft. If the distal tip is lodged into a vascular wall, the lumens of the distal tip may remain unobstructed and able to deliver fluid, monitor cardiac or vascular characteristics, receive fluid, or the like.

The delivery catheter 100 may provide still other features and uses. For instance, cardiac and/or vascular characteristics can be monitored using the delivery catheter boo. Such characteristics may include, for instance, flow rates, beat rates (if any), pressure, or dimensions, or other characteristics. In one example, such as where the delivery catheter 100 is configured to occlude the ascending aorta, the delivery catheter 100 may be adapted to measure a pressure within the aorta, such as the aortic root pressure. As shown in FIGS. 3 and 4, for instance, a secondary lumen 128 may extend to a vent at or near the distal tip 112 of the shaft 102. The secondary lumen 128 may be in fluid communication with a pressure monitoring device (e.g., through a connection at extension arm 118 of FIG. 1), thereby allowing root aortic pressure to be monitored throughout a surgical or other procedure.

The delivery catheter 100 may be configured to provide any number of features. In accordance with some examples, the shaft 102 may be adapted to provide still other features and aspects. For instance, as shown in FIG. 1, the shaft 102 may include one or more markings 122 thereon. Such markings may be bands, ink, radiopaque markers, or otherwise structured to facilitate visualization inside or outside the patient. For instance, in one example, the markings 122 are radiopaque markings that are visible under transesophageal echocardiography visualization or other visualization techniques, so as to facilitate positioning of the shaft within a patient. Where an expandable member 110 is to be placed at a particular location, the expandable member 110 may optionally include additional markings (e.g., platinum-iridium and/or tungsten markers) to facilitate visualization. For instance, as best shown in FIG. 2, one or more markings 140 may be placed on, within, or proximate the expandable member 110 to thereby allow identification of a position of the expandable member 110 when a particular visualization technique is used.

The shaft 102 may be otherwise structured to facilitate insertion, removal, and/or placement of the delivery catheter 100 during a surgical procedure. For instance, as shown in FIGS. 3 and 4, the shaft 102 may include two components. Such components include, in this example, a body element 144 and a core element 130. The body element 144 may, for instance, generally define the shape of the shaft 102 and the lumens 124, 126, 128 within the shaft. In one example, the body element 144 may be formed of any suitable material and using any number of different manufacturing processes. For instance, the body element 144 may be formed from a flexible material that can bend as the shaft 102 translates through a patient's vasculature, to thereby match contours within the patient's body. Suitable materials may include, for instance, ethylene tetrafluoroethylene (ETFE) or poly-tetrafluoroethylene (PTFE). In another example, the body element 144 is formed from another suitable biocompatible material or biocompatible polymer, such as polyether block amide (for example, PEBAX® polyether block amide (Arkema, Colombes, France). A body element 144 formed from polyether block amide can be extruded and can even be extruded to simultaneously define multiple lumens. Accordingly, the body element 144 is optionally a multi-lumen extrusion, although in other examples the body element 144 may be formed as a separate fluid lines layered together with a heat shrink wrap holding them together. In at least some examples, the durometer of the body element 144 may be between about 20 to about 80 Shore D. Such durometer may also change along the length of the body element 144. For instance, the durometer of the distal tip 112 may be lower relative to the durometer at a proximal end of the shaft 102.

In at least some examples, the body element 144 is a solid extrusion, rather than a wrap that includes coils or a supporting exoskeleton, wire frame, or the like. In at least one example, such as that shown in FIGS. 3 and 4, the shaft 102 may include a core 130 within the secondary lumen 126. The secondary lumen 126 may, as discussed previously, be used for facilitating expansion of the expandable member no, or for any other desired feature. The core 130 may be a wire extending along all or a portion of the length of the shaft 102. The core 130 may have a stiffness and strength that provides additional column stiffness to facilitate placement of the shaft 102. The core 130 may additionally, or alternatively, provide kink resistance or define a desired shape of the shaft 102.

For instance, as reflected in FIG. 1, the distal end 108 of the shaft 102 may have a bend, curve, or other shape. In some examples, the shaft 102 may be configured to pass through the descending aorta and into the ascending aorta. To do so, the curved distal end 108 may pass around a relatively tight curve radius, namely the curve radius defined by the aortic arch.

While curvature of the distal end 108 may be produced by allowing the body element 144 and/or core 130 to be made of a flexible material, in other examples the core is pre-designed and manufactured to maintain a specific curved profile. In still other examples, such curved profile may be selectively activated in the shaft 102. To obtain these and other characteristics, in one example, the core 130 can be comprised of biocompatible materials that are at least temporarily deformable. Suitable biocompatible materials can include, for example, superelastic and/or shape memory materials (e.g., copper-zinc-aluminum; copper-aluminum-nickel; nickel-titanium alloys known as nitinol; cobalt-chromium-nickel alloys, cobalt-chromium-nickel-molybdenum alloys, nickel-titanium-chromium alloys, and the like). In addition, other suitable materials may include stainless steel, silver, platinum, tantalum, palladium, cobalt-chromium alloys, niobium, iridium, any equivalents thereof, alloys thereof or combinations thereof. Further details of the shaft curvature and examples of the core can be found, for example, in U.S. Pat. No. 10,130,371, which is incorporated herein by reference in its entirety for all purposes.

In some examples, the core 130 may be a wire, although the core 130 may take other forms. As illustrated in FIG. 4, the core 130 may be a wire having a variable cross-sectional shape. In particular, in at least one example, the core 130 may have a distal end 142 at least proximate the distal end 108 of the shaft 102. As the core 130 approaches the distal tip 112 of the shaft 102, the size of the core 130 may, in some examples, decrease, such as by having a tapered, stepped, or other configuration. In such a manner, the strength of the core 130 at the distal tip 112 may be decreased, thereby also reducing the force that the core 130 can exert at the distal tip 112. With reduced force at the distal tip 112, trauma to a patient's vasculature may be decreased.

The shaft 102 and the hub 104 may be formed in any number of manners, or have any other number of features or configurations. For instance, the size of the shaft 102 may be varied as desired. In accordance with one example, the shaft 102 may have an outer diameter of between about eight and ten French, so as to be passable from a peripheral artery through the descending aorta, and into the ascending aorta as described herein. Depending on other uses of the delivery catheter 100, the patient with whom the catheter 100 is used, or other factors, the size of the shaft 102 may be larger than ten French, or smaller than eight French.

The shaft 102 may be connected to the hub 104 in any suitable manner. For instance, in one example, the shaft 102 and the hub 104 are an integral unit and are molded together. In another example, the shaft 102 may be formed separate from the hub 104 and thereafter attached to the hub. For instance, the shaft 102 may be extruded and the hub 104 may be molded and then bonded to the shaft 102. Such bonding may be performed by a thermal bonding, overmolding, adhesive, or other attachment procedure. The extension arms 114, 116, 118, 120 may be similarly formed. For instance, the extension arms 114, 116, 118, 120 may be molded and integrally formed with the hub 104. In some examples, the extension arms 114, 116, 118, 120 are flexible, but may be rigid. In at least one example, some extension arms (e.g., arms 116, 118) may be flexible while other extension arms (e.g., arms 114, 120) are substantially rigid. As discussed herein, the extension arms 114, 116, 118, 120 with access ports 115, 117, 119, 121 may serve as ports and facilitate balloon inflation, aortic root pressure monitoring, cardioplegia delivery, aortic root venting, or other aspects.

In at least one example, the hub 104 may further facilitate proper positioning of the distal end 108 of the shaft 102 within a patient. For instance, as discussed previously, the shaft 102 may have a predetermined curve or other profile. The predetermined curve or other profile may be fixed in relation to the orientation of the hub 104. Indicia (not shown) may be placed on the hub 104 to indicate the direction of the curved profile of the shaft 102 such that once the distal end 108 of the shaft 102 is within a patient, the physician or other operator will be aware by glancing at the hub 104 as to what direction the shaft 102 will bend or curve. In other examples, the hub 104 may be asymmetric. A direction of asymmetry may correspond with the curve of the shaft 102, thereby allowing the physician to glance at the hub 104, view the asymmetry, and know which direction the shaft 102 curves.

Figures 5, 6, 7:
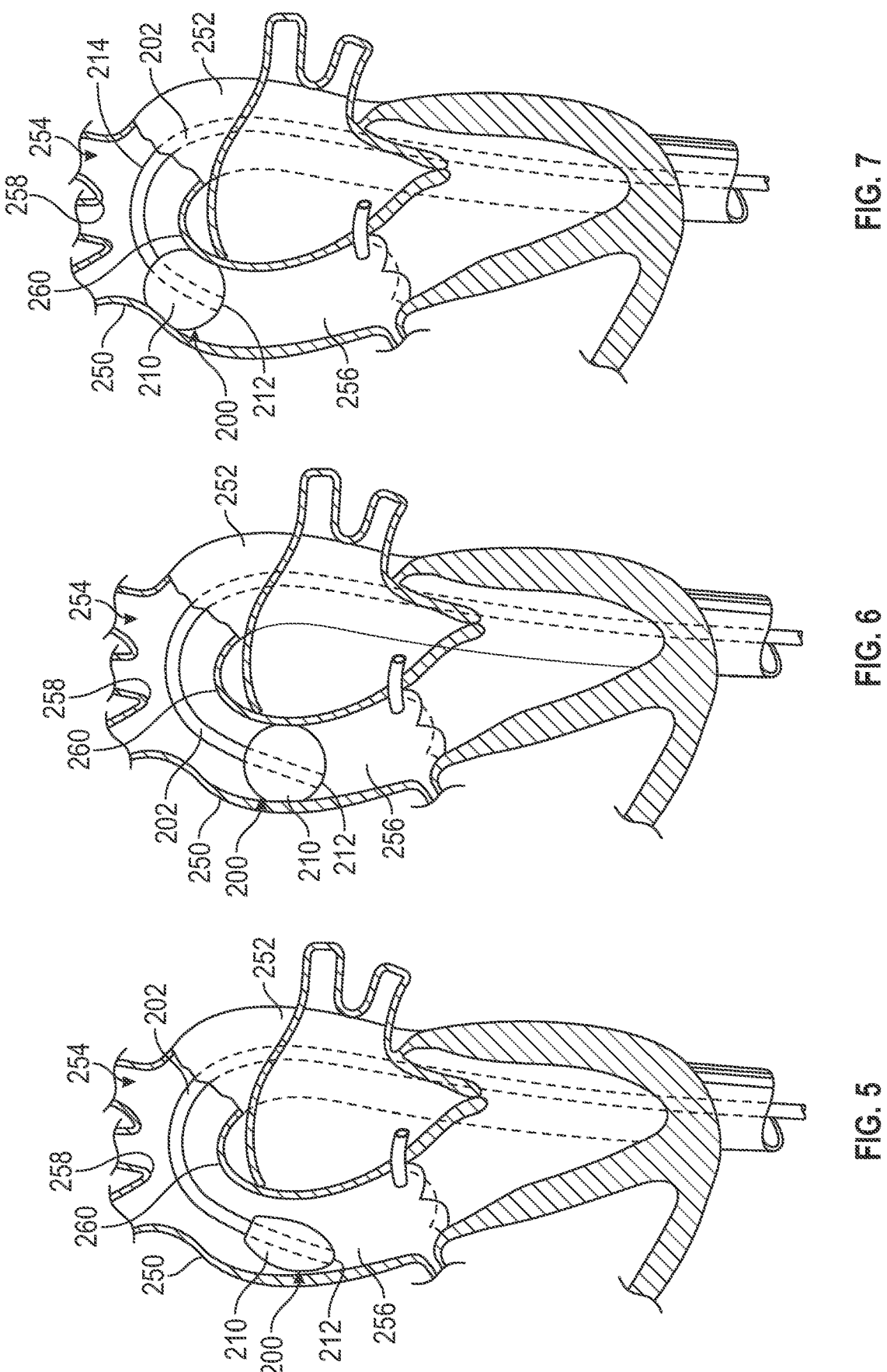
FIG. 5-7 are partial cross-sectional views of the distal end of a catheter assembly configured as an antegrade cardioplegia delivery catheter used to occlude a portion of the ascending aorta.

Referring now to FIGS. 5-7, an exemplary catheter assembly configured as an aortic occlusion assembly 200 can be used to occlude a selected occlusion site (e.g., a patient's aorta 250) in the following exemplary manner. FIGS. 5-7 generally illustrate a process of inserting a shaft 202 and expandable member 210 of a delivery catheter into a patient's aorta 250, expanding the expandable member 210, and retracting the expandable member 210 to secure the expandable member 210 in an occluding position. FIGS. 5-7 represent one method of using the delivery catheter boo. Thus, in one example, the shaft 202 corresponds to the shaft 102 and the expandable member 210 corresponds to the expandable member 110.

More particularly, in FIG. 5, a shaft 202 and expandable member 210 may be passed through the descending aorta 252, around the aortic arch 254, and into the ascending aorta 256. During such movement, the expandable member 210 may be in a deflated or otherwise contracted state. In order to facilitate placement of the expandable member 210 and a distal tip 212 within the ascending aorta 256, the shaft 202 may be flexible. In particular, the shaft 202 may bend to generally correspond to a curve of the aortic arch 254. For instance, the aortic arch 254 may have an upper profile 258 and a lower profile 260. The shaft 202 may bend so as to generally have a curve that extends partially between the upper and lower profiles 258, 260 of the aortic arch 254.

The expandable member 210 and distal tip 212 may be located using any suitable visualization technique. Once positioned in the desired location, the expandable member 210 may be expanded using any suitable manner, including those described herein. For instance, the expandable member 210 may be a balloon that is inflated to substantially occlude the ascending aorta 256. In FIG. 6, for instance, the expandable member 210 has a generally spherical shape and the shaft 202 is generally concentric within the expandable member 210.

Inflation of the expandable member 210 on the distal end of the shaft 202 can fix the distal tip 212 of the shaft 202 within the ascending aorta 256 and isolate the left ventricle of the heart and the upstream portion of the ascending aorta 256 from the rest of the arterial system downstream from the expandable member 210. The passage of any debris or emboli, solid or gaseous, generated during a cardiovascular procedure to regions downstream from the site can be substantially prevented by the expanded expandable member 210. Fluid containing debris or emboli can be removed from the region between the aortic valve and the occluding expandable member 210 through an interior lumen of the shaft 202. A clear, compatible fluid (e.g., an aqueous based fluid such as saline) delivered through an interior lumen or the cardioplegic fluid may be maintained in the region wherein the cardiovascular procedure is to be performed to facilitate use of an angioscope or other imaging means that allows for direct observation. Such use of a delivery catheter may be particularly useful in the removal of an aortic heart valve and replacement thereof with a prosthetic heart valve which procedure is described in U.S. Pat. No. 5,738,652, which is incorporated herein by reference in its entirety for all purposes.

The expandable member 210 may have forces applied thereto that cause the expandable member 210 to shift position. For instance, as cardioplegic fluid is expelled from the distal tip 212 the fluid flow may generally cause the expandable member 210 to move upward through the ascending aorta 256 and towards the aortic arch 254. Other forces may also be applied, for instance, a decrease in perfusion pressure may also cause the expandable member 210 to move towards the aortic arch 254. In contrast, the systemic blood pressure, increases in root vent suction, or increases in perfusion pressure may tend to cause the expandable member 210 to move further into the ascending aorta 256 and away from the aortic arch 254.

Migration of the expandable member 210 may be particularly likely where slack is present in the shaft 202. Accordingly, to minimize migration of the expandable member 210, a surgeon may pull on the delivery catheter so as to at least partially retract the shaft 202. For instance, a surgeon may pull two to three inches of slack out of the shaft 202. As a result, the expandable member 210 may move towards the aortic arch 254. In retracting the expandable member 210, external surfaces of the expandable member 210 may also more fully engage the upper and lower portions of the ascending aorta 256, thereby more securely positioning the expandable member 210 as it occludes the aorta.

As shown in FIG. 7, the shaft 202 may have a curved profile 214 that generally corresponds to a portion of the aortic arch 254. In this example, for instance, the curved profile 214 allows the shaft 202 to curve around the aortic arch 254 generally between the upper profile 258 and lower profile 260 of the aortic arch 254. The shaft 202 may be generally mid-way between the upper and lower profiles 258, 260, although such is not necessary. For instance, the shaft 202 may be generally flexible such that the profile 214 adapts to a suitable geometry that allows the expandable member 210 to remain at the illustrated occluding position.

When the slack is pulled from the shaft 202, such that the expandable member 210 is secured within the ascending aorta 256, the distal tip 212 of the shaft 202 may migrate and change orientation within the ascending aorta 256. More particularly, in the illustrated example, the distal tip 212 may be positioned at an angle relative to the ascending aorta 256. As noted herein, cardioplegic fluid may, in some instances, be perfused to the ascending aorta 256 through the distal tip 212. Generally speaking, the shape of the expandable member 210, curvature of the shaft 202, and location of the shaft 202 within the expandable member 210 may each contribute to the orientation of the distal tip 212.

Once the expandable member (e.g., expandable member 110 or 210) is positioned at a selected position within the body (e.g., within the ascending aorta 256), the physician can engage a clamping device, such as clamping device 103 of delivery catheter 100, to prevent or minimize movement of the expandable member relative to the selected position and movement of the shaft relative to the aorta.

Figure 8:
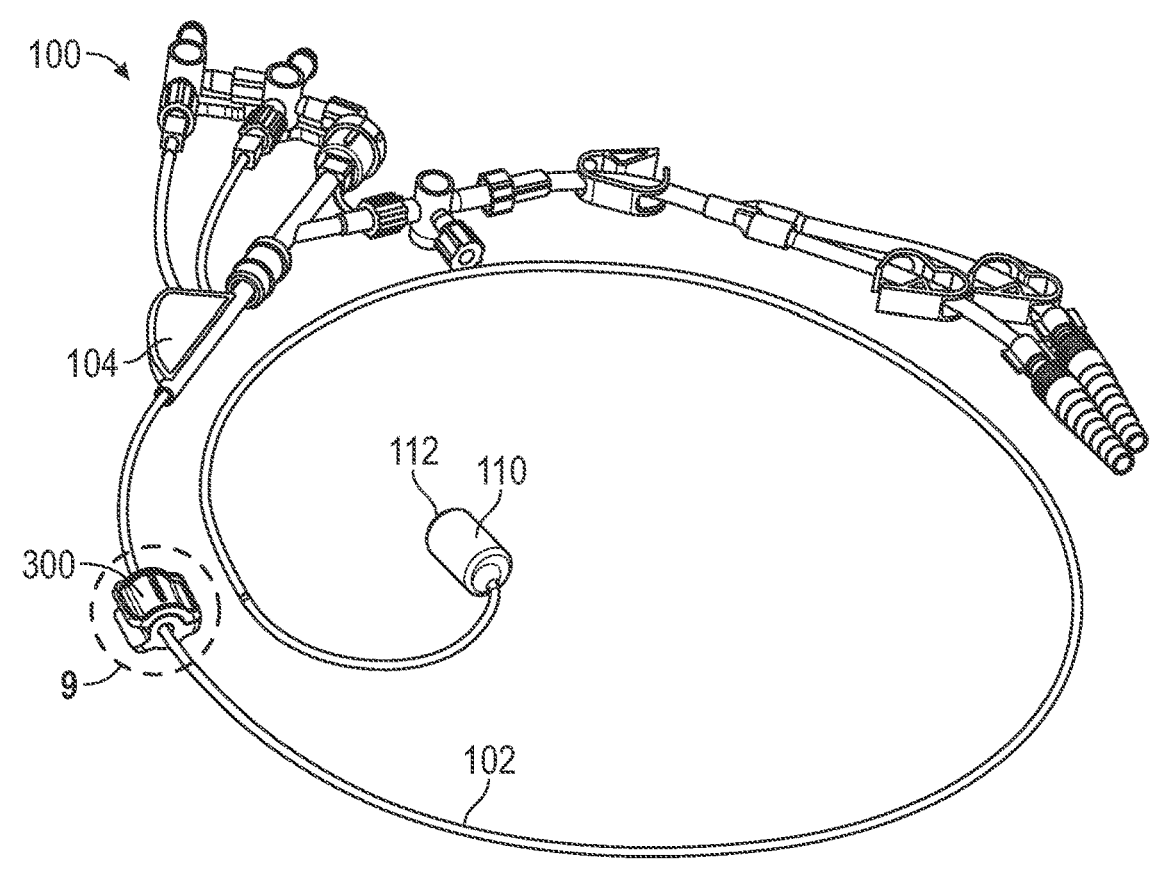
FIG. 8 is a perspective view of an exemplary catheter assembly configured as an antegrade cardioplegia delivery catheter including an exemplary clamping device.
Figure 9:
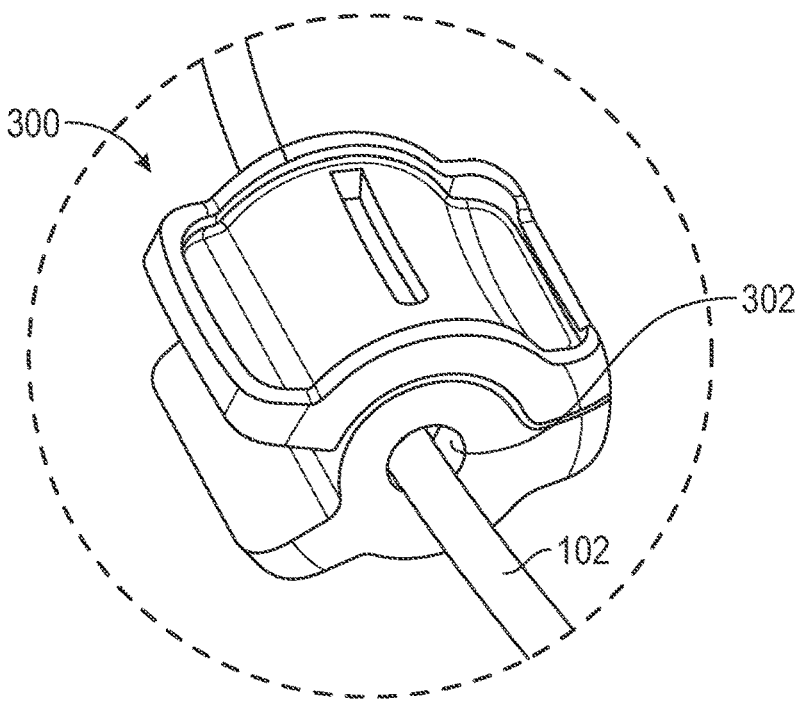
FIG. 9 is a perspective view of the clamping device of FIG. 8.

As shown in FIG. 8, an exemplary clamping device 300 can be used with a delivery catheter, such as delivery catheter 100 described above. For instance, a clamping device can be used to prevent movement of an expandable member (e.g., expandable member no) relative to a patient's aorta. Referring now to FIG. 9, the shaft 102 of the delivery catheter 100 can extend through a central lumen 302 of the clamping device 300. The clamping device 300 can be movable between an unclamped or release state wherein the clamping device can be moved along the length of the shaft 102 and a clamped state wherein the clamping device 300 engages and clamps onto an outer surface of the shaft 102, thereby preventing movement of the clamping device 300 and the shaft 102 relative to one another, as described in more detail below.

Figure 10:
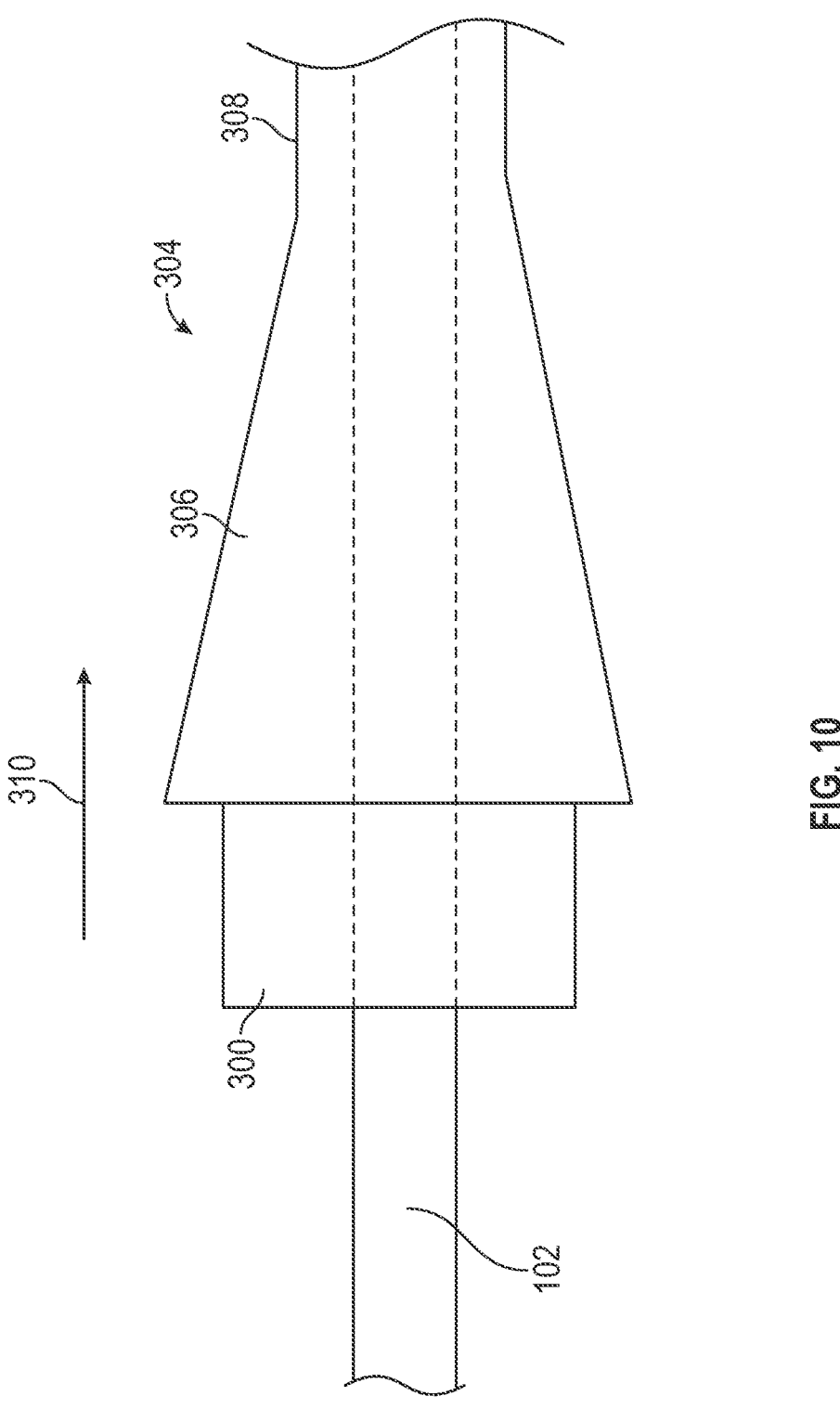
FIG. 10 is a side elevation view of an exemplary catheter assembly including an exemplary clamping device and an introducer.

In some examples, as shown in FIG. 10, in the clamped state, the clamping device 300 can abut a proximal end of a hub 306 of an introducer assembly 304. In use, an elongated sheath 308 of the introducer assembly 304 is inserted into a blood vessel of the patent (e.g., a femoral artery) and the delivery catheter 100 is inserted through the introducer assembly into the blood vessel. The diameter of the clamping device is greater than the diameter of a proximal opening of the hub 306, preventing the portion of the shaft on which the clamping device is mounted from passing through the introducer and into the patient's body when the clamping device is in the clamped state. The clamping device 300 can bear against the introducer assembly and thereby mitigate movement of the shaft 102 relative to the introducer assembly 304 in the distal direction 306. Mitigating movement of the shaft 102 relative to the introducer assembly 304 thereby mitigates movement of the distal end portion of the shaft 102 within the patient's body.

Figure 11:
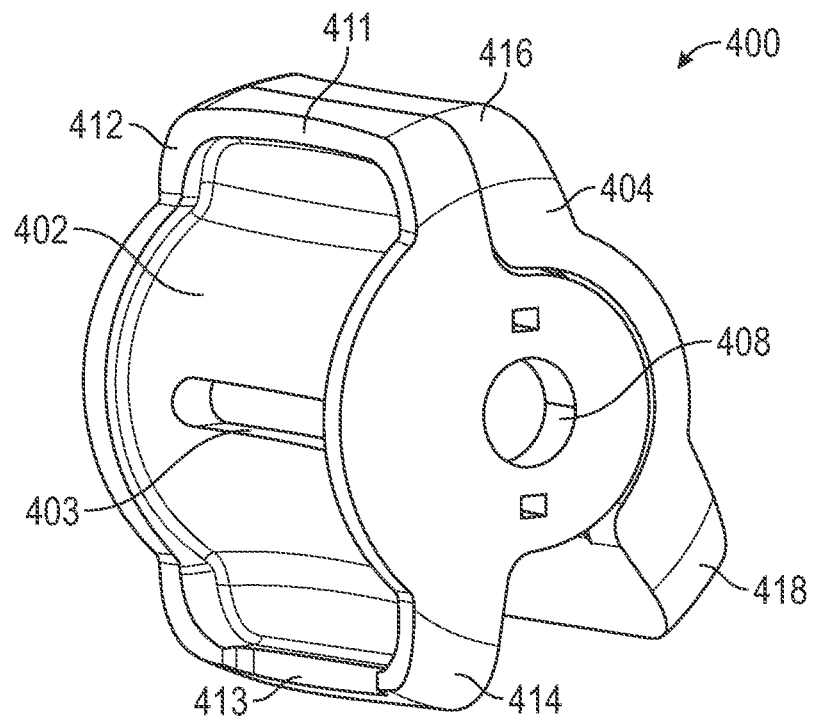
FIGS. 11-12 are perspective views of an exemplary clamping device.
Figure 12:
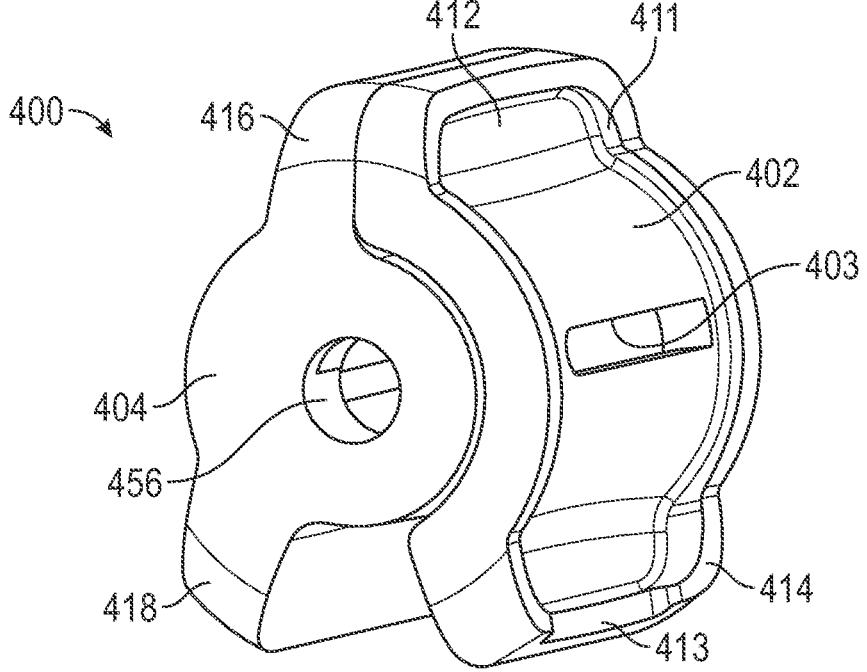

FIGS. 11-20 illustrate a representative example of a clamping device 400. As shown in FIG. 11, the clamping device 400 can comprise three main components: a first member 402, a second member 404, and an elastomeric member 406 (see FIG. 18). The first and second members 402, 404 can be rotatably coupled to one another, and can be axially fixed relative to one another. The first and second member 402, 404 can define a central lumen 408 extending longitudinally through the clamping device 400. The elastomeric member 406 can be a tubular member defining a second lumen 410 through which a shaft of the delivery catheter, such as shaft 102, can extend. The elastomeric member 406 can be disposed within the central lumen 408, as described in more detail below.

Figure 13:
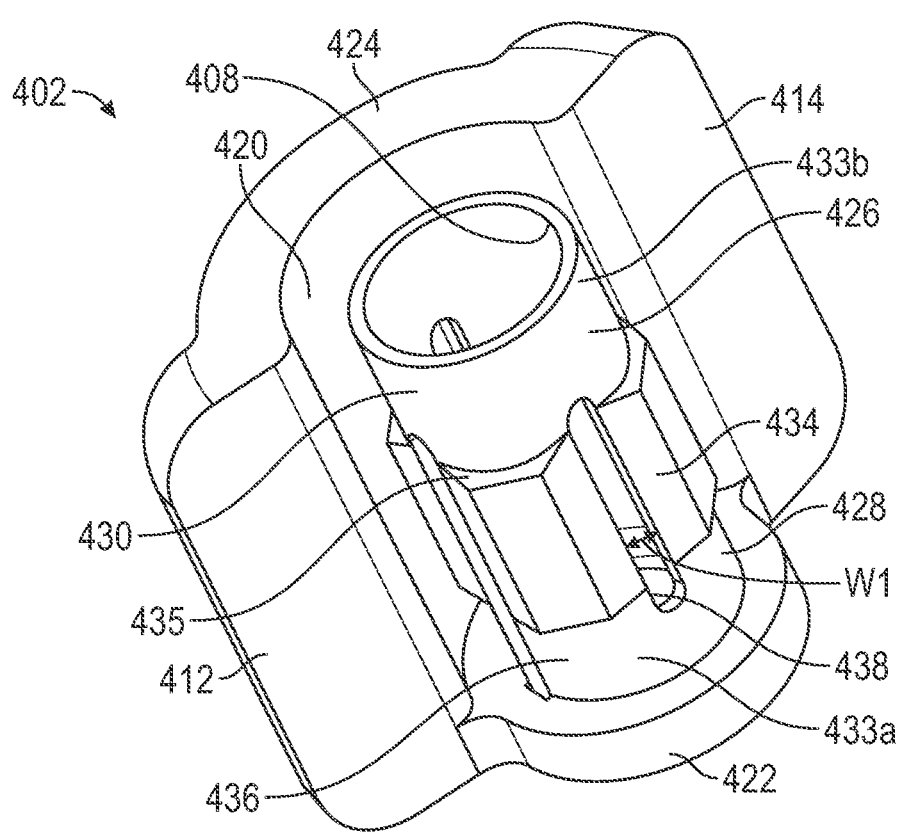
FIG. 13 is a perspective view of a first portion of the clamping device of FIGS. 11-12.
Figure 14:
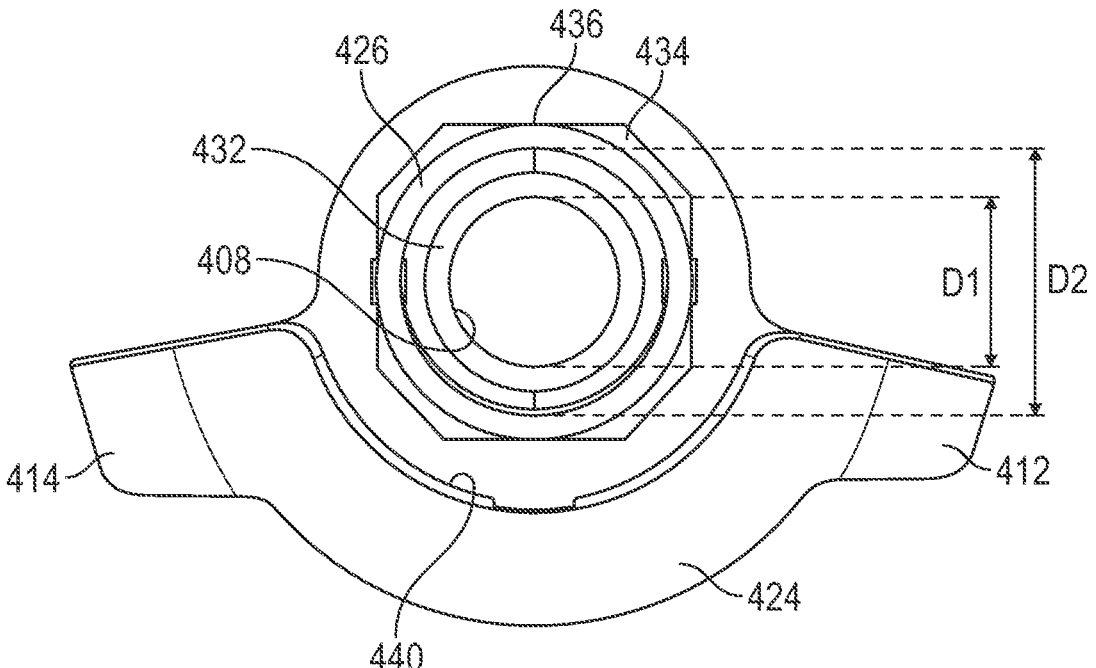
FIG. 14 is an end view of the first portion of the clamping device of FIG. 13.
Figure 15:
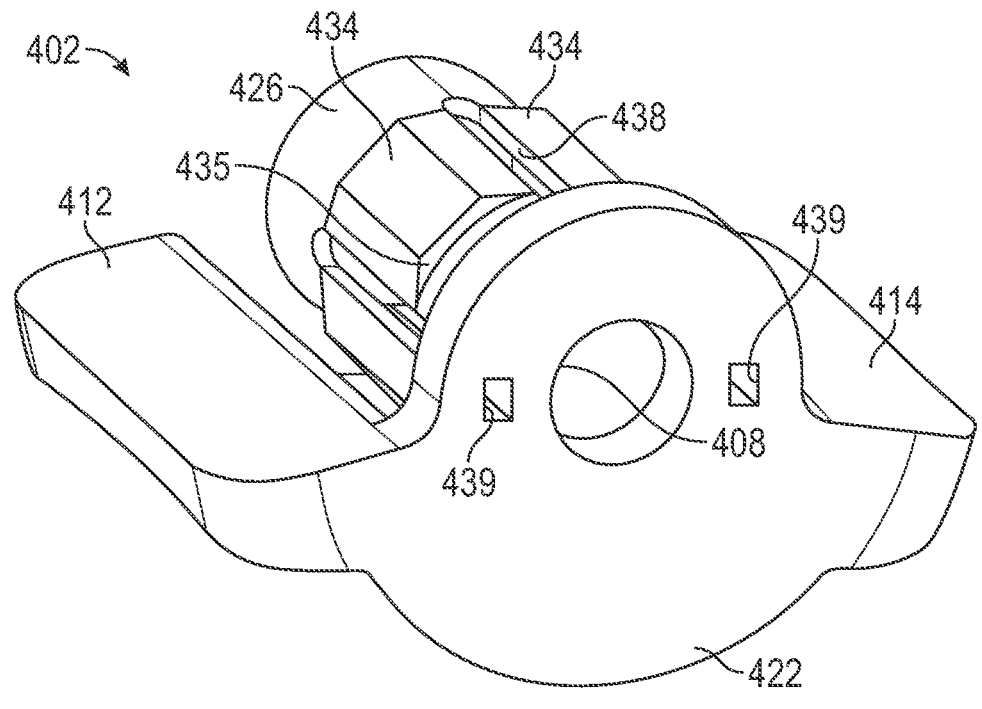
FIG. 15 is a perspective view of the first portion of the clamping device of FIG. 13.

Referring now to FIGS. 13-15, the first member 402 can comprise a body 42o having a first end portion 422 and a second end portion 424. In some examples, the first member 402 can have first and second extension portions 412, 414 extending from the body 420.

An annular element 426 can extend longitudinally from the first end portion 422 toward the second end portion 424 and can define the central lumen 408. In some examples, the annular element 426 can be formed integrally with the body 420, in other examples the annular element 426 can be formed separately and coupled to the body 420 in various other ways, such as by snap-fit, thermal bonding, overmolding, adhesive, mechanical means such as screws, and/or other means of coupling.

Figure 18:
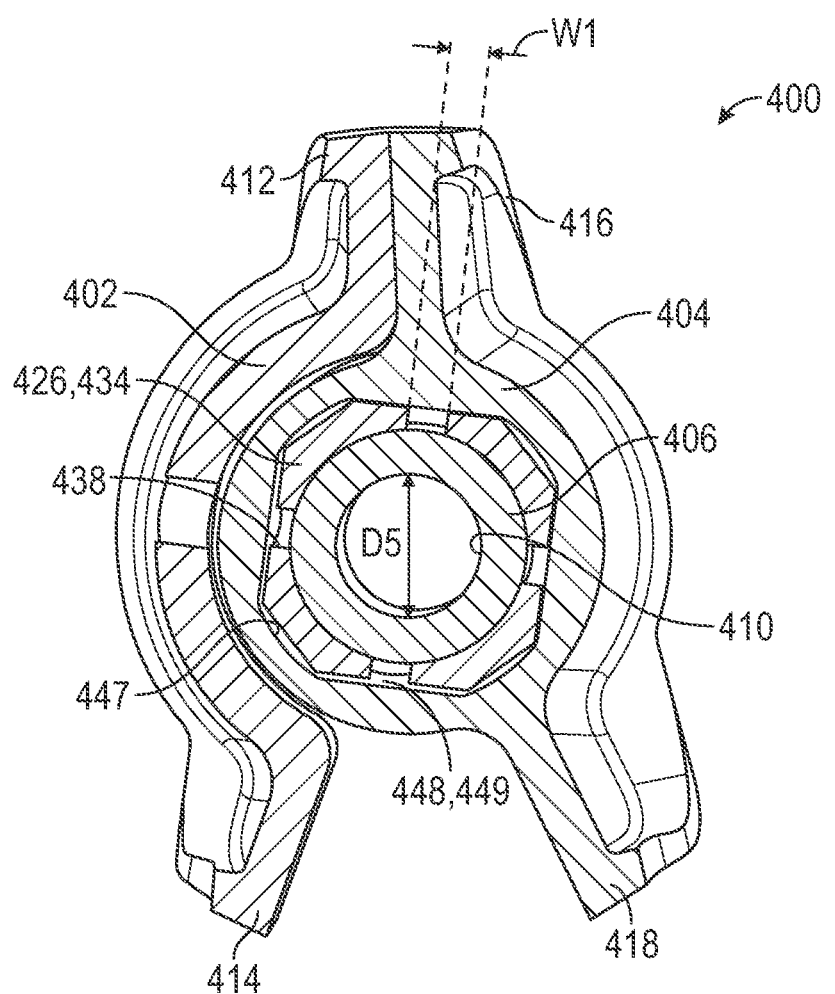
FIG. 18 is a transverse cross-sectional view of the clamping device of FIG. 11 where the clamping device is in the release state.

As shown in FIG. 14, the annular element 426 can have a first end portion 428 coupled to the first end portion 422 of the body 420 and a second, free end portion 430. The first end portion 428 can comprise an annular lip 432 (see e.g., FIG. 14) extending into the central lumen 408 such that the central lumen has a first diameter $D_1$ at the first end portion, and a second, greater diameter D2 at the second end portion 430. The first diameter $D_1$ can be sized to allow a shaft of a delivery system to extend through the central lumen 408. The annular lip 432 can help retain the elastomeric member 406 within the annular element 426 when the clamping device 400 is assembled, as shown in FIG. 18.

The annular element 426 can comprise one or more engagement members 434 (e.g., four in the illustrated example). The engagement members 434 can extend longitudinally along the annular element 426 from a first cylindrical portion 433a to a second cylindrical portion 433b of the annular element, and can be spaced apart from each other about a circumference of the annular element 426. As shown in FIG. 14, the engagement members 434 can protrude radially outward from outer surfaces 436 of the cylindrical portions 433a, 433b to define a non-circular cross-sectional profile of the annular element 426 (the cross-sectional profile being taken perpendicular to the longitudinal axis of the annular element). When the clamping device 400 is in the clamped state, the engagement members 434 can deflect inwardly toward the central lumen 408. The engagement members can have end surfaces 435 configured to abut portions of the second member 404 and form a snap-fit connection between the first member 402 and the second member 404, as described in more detail below.

In the illustrated example, the engagement members 434 are chamfered rectangular protrusions. However, in other examples, the engagement members 434 can have other shapes, including but not limited to cuboid, elliptical, ovular, triangular, etc. Such shapes can also comprise chamfered portions.

Though the illustrated example shows four engagement members, in other examples, the annular element can comprise a greater or fewer number of engagement members. For example, in some examples, the annular element can comprise one, two, three, or five engagement members.

The annular element 426 can further comprise one or more slots or openings 438 (e.g., four in the illustrated example) extending through a thickness of the annular element 426 and extending longitudinally along the annular element 426. The openings 438 can be spaced apart about the circumference of the annular element 426. The openings 438 allow the annular element 426 to deflect radially inwardly when a compressive force is applied to an outer surface of the annular element 426.

In some examples, the openings 438 can have differing sizes. For example, one or more of the openings (e.g., two in the illustrated example) can extend through the first end portion 422 of the body 420 to form openings 439 in the first end portion (FIG. 15). The one or more openings 438 can have a first width $W_1$ when the clamping device 400 is in the release state, and a second width $W_2$ (see FIG. 19) when the clamping device is in the clamped state. In the illustrated example, the first and second widths $W_1$, $W_2$ are the same for each opening, however, in other examples, the widths may vary between openings.

Though the illustrated example shows four openings 438, in other examples, the annular element can comprise a greater or fewer number of openings. For example, in some examples, the annular element can comprise one, two, three, or five openings.

The body 420 can have a curved shape between the first and second extension portions 412, 414 such that a curved space is defined between the outer surface 436 of the annular element 426 and an inner surface 440 of the body 420. The curved space can be sized to accept a wall of the second member 404, such that the first and second members 402, 404 can form a snap-fit connection, as described in more detail below.

In the illustrated example, the first member 402 comprises a slot 403 extending through a thickness of the body portion 420 and extending longitudinally along the length of the body portion. The slot 403 can allow the first and second members 402, 404 to more easily rotate relative to one another.

Figure 16:
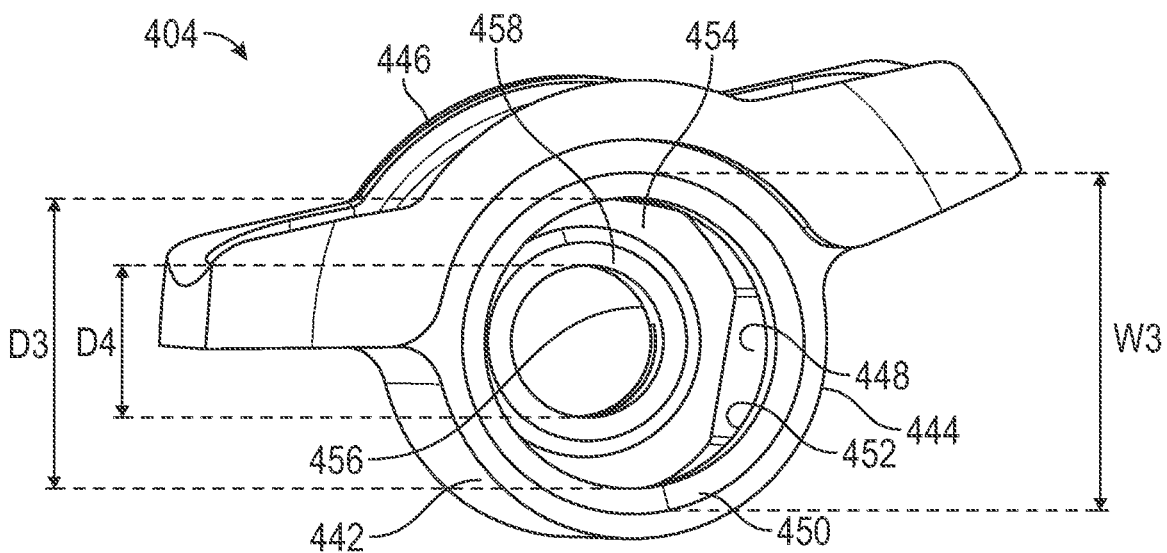
FIGS. 16-17 are perspective views of a second portion of the clamping device of FIGS. 11-12.
Figure 17:
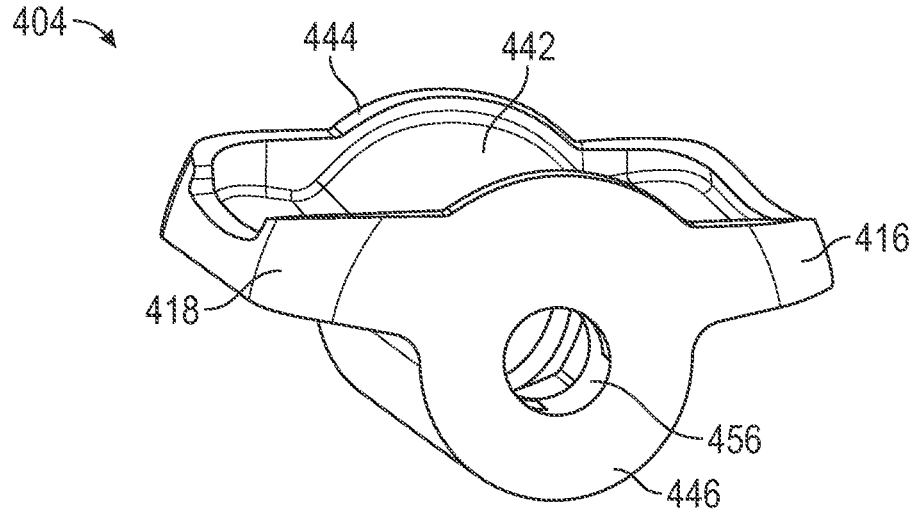

Referring now to FIGS. 16 and 17, the second member 404 can comprise a body 442 having a first end portion 444 and a second end portion 446 and defining a bore 448 extending longitudinally along the length of the second member 404. As shown in FIG. 16, the bore 448 can have a non-circular cross-section having a shape that generally corresponds to the shape of the non-circular cross-section of the annular element 426 when the bore 448 and the annular element 426 are rotationally aligned, as described in more detail below. In the illustrated example, as can be seen in the cross-sectional view shown in FIG. 18, the cross-sectional profile of the bore 448 (taken in a plane perpendicular to the longitudinal axis of the second member and the bore 448) comprises a substantially square shape including rounded corner portions 447 and flat side portions 449. However, in other examples, the annular element and the bore can have any of various corresponding non-circular shapes in cross-section including, but not limited to, elliptical, triangular, rectangular, cruciform (cross-shaped), flat-oval shaped (e.g., a shape comprising an oval with flat sides), etc.

The second member 404 can have one or more annular lips. The first end portion 444 can have a first annular lip 450 extending radially inward toward the bore 448 to define an opening 452 having a first diameter $D_3$ at the first end portion. The second end portion 446 can have a second annular lip 454 extending radially inward toward the bore 448 and defining an opening 456 having a second diameter $D_4$ smaller than the first diameter $D_3$. The second annular lip 454 can comprise an annular protrusion 458 extending toward the first end portion 444 (see FIG. 20). An annular space can be formed between the annular protrusion 458 and the bore 448. The outer diameter of the annular protrusion 458 can be less than the inner diameter of the annular element 426 such that the annular protrusion 458 can extend into the annular element 426 when the clamping device 400 is assembled.

The non-circular portion of the bore 448 extending between the first and second annular lips 450, 452 can have a width $W_3$ greater than both the first and second diameters. This configuration allows the annular element 426 to be inserted into the bore 448 in a snap-fit connection, as described in more detail below.

Referring again to FIGS. 11 and 12, in some examples, the first member 402 can have first and second extension portions 412, 414 and the second member 404 can have first and second extension portions 416, 418. The extension portions 412, 414, 416, 418 can be oriented as opposing pairs. For example, in the illustrated example, extension portions 412 and 416 can form a first pair and extension portions 414 and 418 can form a second pair. The extension portions 412, 414, 416, 418 can be actuated by a physician to rotate the first and second members 402, 404 relative to one another, thereby moving the clamping device between the release state and the clamped state. For example, when extension portions 412 and 416 abut one another, the clamping device 400 is in the release state, and when extension portions 414 and 418 abut one another, the clamping device is in the clamped state (see FIG. 19). The release and clamped states are described in more detail below with reference to FIGS. 18-19.

In some examples, each member 402, 404 can comprise a respective ridge 411 on an outer surface of the member. Each ridge 411 can extend along a perimeter of the outer surface of the member 402, 404. The ridge 411 can facilitate a physician's grip on the clamping device 400.

In some examples, one or more of the opposing pairs of extension portions can comprise indicia configured to indicate to a physician that actuating that opposing pair of extension portions will move the clamping device from the release state to the clamped state, or vice versa. For example, in the illustrated example, the clamping device is in the clamped state when extension portions 414 and 418 abut one another. Accordingly, extension portions 414 and 418 can each comprise indicia 413. The indicia 413 can be, for example, tactile indicia (e.g., a surface texture, a raised marking, a cutout, a portion of the extension portion being formed from a different material, etc.) and/or visual indicia (e.g., the extension portions can be a different color, or can comprise markings, etc.). In the illustrated example, the indicia 413 are cutouts in the ridge 411, a physician can feel the cutouts and determine which extension portions must be actuated to move the clamping device to the clamped state. In some examples, the indicia can be formed integrally with the extension portions. Alternatively, the indicia can be formed separately and bonded with the extension portions, such as by thermal bonding, adhesive, laser welding, over-molding, and/or mechanical means such as screws, etc.

Referring now to FIG. 18, which illustrates a transverse cross-section of the clamping device 400 of FIG. 11, the elastomeric member 406 can be positioned within the central lumen 408 of the annular element 426. In the illustrated example, the elastomeric member 406 is a cylindrical, tubular member. However, in other examples, the elasto-meric member can take any of various forms having an outer profile corresponding to the inner profile of the annular element 426. The elastomeric member 406 can define a lumen 410 extending along the length of the elastomeric member. The lumen 410 can be sized to receive the shaft of a medical instrument, for example, a delivery catheter. When the clamping device is in the release state the lumen 410 can have a first diameter $D_5$ such that the clamping device can be moved along the length of the catheter shaft, and when the clamping device is in the clamped state (e.g., FIG. 19) the lumen 410 can have a second diameter $D_6$ smaller than the first diameter. The second diameter $D_6$ can be sized to engage the surface of the shaft such that the clamping device 400 and the shaft are restrained from movement relative to one another.

In particular examples, the elastomeric member 406 can comprise natural rubber, any of various synthetic elasto-mers, such as silicone rubber or polyurethane, or various combinations thereof.

The outer diameter of the elastomeric member 406 can be slightly smaller than the inner diameter of the annular element 426 such that the elastomeric member 406 is retained within the annular element 426. The elastomeric member 406 can be restrained from sliding out of the annular element by annular lip 432 of the first member 402 and by the annular lip 454 and/or annular protrusion 458 of the second member 404.

Figures 19, 20:
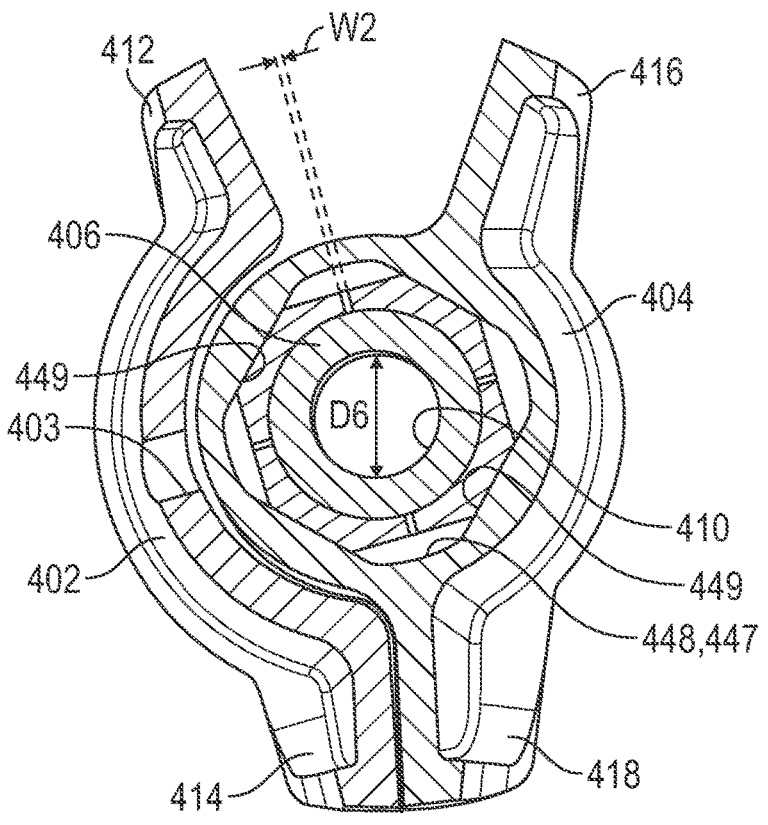
FIG. 19 is a transverse cross-sectional view of the clamping device of FIG. 11 where the clamping device is in the clamped state.
FIG. 20 is a top down cross-sectional view of the clamping device of FIG. ii with the elastomeric member removed.

When the clamping device 400 is assembled, the annular element 426 of the first member 402 can extend into the bore 448 of the second member 404 in a snap-fit connection. As the annular element 426 is inserted into the bore 448, the first annular lip 450 of the second member 404 can deflect the engagement members 434 radially inward, compressing the annular element 426 (and therefore the elastomeric member 406) to a reduced diameter such that the annular element 426 can pass through the opening 452 defined by the first annular lip 450. Once the engagement members 434 have passed through the opening 452, the annular element 426 can return to its uncompressed diameter within the bore 448. As the uncompressed external diameter of the annular element 426 (including engagement members 434) is greater than the diameter of the opening 452, the annular element 426 is retained within the bore 448. The end surfaces 435 (see e.g., FIG. 15) of the engagement members 434 can abut the annular lip 450, restraining the first and second members 402, 404 from axial movement relative to one another. As shown in FIG. 20, the annular protrusion 458 of the second member 404 can extend into the central lumen 408 of the annular element 426 such that the second end portion 430 of the annular element 426 is retained between the annular protrusion 458 and the bore 448.

Thus assembled, the first member 402 and the second member 404 are fixed axially relative to one another and can be rotated relative to one another to move the clamping device 400 between the release state and the clamped state.

In the illustrated example, the first and second members 402, 404 can be rotated relative to one another by actuating either pair of extension portions 412 and 416 or 414 and 418, respectively. The extension portions can be actuated by applying opposing forces to a pair of extension portions such that the extension portions move toward one another and abut one another (e.g., by pinching the extension portions together). This configuration allows a physician to quickly and easily move the clamping device between the release state and the clamped state. For example, a physician can move the clamping device into the clamped state (see e.g., FIG. 19) by pinching extension portions 414 and 418 until they abut one another and can move the clamping device into the release state by pinching portions 412 and 416 until they abut one another.

In some examples, the clamping device can be sized such that a physician can pinch the extension portions together using only one hand. In other examples, the clamping device 400 can be actuated in any of various ways that cause the first and second members 402, 404 to move relative to one another. For example, a physician can restrain the first member 402 from movement while rotating the second member 404, or vice versa.

Referring again to FIG. 18, when the clamping device 400 is in the release state, the bore 448 and the outer surface of the annular element 426 are rotationally aligned. As used herein, the term "rotationally aligned" means that the annu-lar element 426 is in a first rotational position relative to the bore 448 such that the cross-sectional profile of the annular element corresponds to the cross-sectional profile of the bore 448. In other words, the annular element 426 (and therefore the elastomeric member 406) is not compressed or deflected by the bore 448. In the illustrated example, when the bore and the annular element are rotationally aligned, the engage-ment members 434 of the annular element 426 extend into the rounded corner portions 447 of the bore 448 and the openings 438 in the annular element 426 have a first width $W_1$. In the rotationally aligned state, the lumen 410 has a first diameter $D_5$ sized such that the clamping device 400 is movable relative to a shaft extending through the lumen 410.

Referring now to FIG. 19, when the clamping device 400 is in the clamped state, the bore 448 and the outer surface of the annular element 426 are rotationally offset. As used herein, the term "rotationally offset" means that the annular element 426 is in a rotational position relative to the bore 448 such that the cross-sectional profile of the annular element does not correspond to the cross-sectional profile of the bore. In this position, the cross-sectional profile of the bore 448 exerts a compressing force on the annular element 426 (and therefore on the elastomeric member 406). In the illustrated example, when the bore and the annular element are rotationally offset, the flat side portions 449 of the bore 448 contact the engagement members 434, deflecting the engagement members radially inward toward the lumen 410. As the engagement members 434 are deflected inwardly they move toward one another such that the openings 438 narrow to a second width $W_2$ and such that the lumen 410 narrows to a second diameter $D_6$. In the rotationally offset state, the second diameter $D_6$ is sized such that the internal surface of the elastomeric element 406 engages the outer surface of a shaft extending through the lumen 410. The frictional force of the elastomeric element 406 against the outer surface of the shaft is sufficient to resist longitudinal movement of the shaft relative to the clamping device, and vice versa.

In alternative examples, the clamping device 400 does not include an elastomeric member 406 and instead inner surface portions of the annular element 426 can clamp against and grip the outer surface of the shaft. For example, the annular element 426 can be sized that the inner surfaces of the engagement members 434 can come into contact with the outer surface of the shaft when clamping device 400 is in the clamped state. In some examples, a thin layer of an elastomeric material (e.g., silicone rubber) can be secured, such as with an adhesive, to the inner surface of each engagement member 434, and the layers of elastomeric material can come into contact with the outer surface of the shaft when clamping device 400 is in the clamped state.

The clamping device 400 can be used to restrict movement of a shaft of a first medical device relative to another medical device through the shaft extends. For example, while the clamping device 400 is in the release state, a physician can slide the clamping device 400 along the shaft of the first medical device until the clamping device reaches a selected clamping site. In some examples, for example, the selected clamping site can be adjacent the proximal end portion of a second medical device through which the first medical device extends.

Once the clamping device is positioned at the selected clamping site, the physician can actuate the clamping device 400 to move the device from the release state to the clamped state. For example, the physician can apply force to extension portions 414 and 418 such that the first member 402 and the second member 404 rotate relative to one another and extension portions 414 and 418 abut one another. As the annular element 426 rotates into the rotationally offset position relative to the bore 448, the annular element 426 (and therefor the elastomeric member 406) is compressed by the bore 448, thereby reducing the lumen 410 of the elastomeric element 406 from the first diameter $D_5$ to the second diameter $D_6$. When compressed to the second diameter $D_6$, the inner surface of the elastomeric element 406 frictionally engages the outer surface of the shaft, preventing the clamping device 400 from moving relative to the shaft. Thusly clamped to the shaft, the clamping device 400 abuts the proximal end of the second medical device and prevents distal movement of the first shaft relative to the second medical device.

The first medical device can comprise any medical device comprising a shaft, including, but not limited to, a catheter (e.g., catheter 100), a cannula, a needle or a medical probe. The second medical device can be any medical device that has an opening or bore sized to receive the shaft of the first medical device.

In one specific implementation, as depicted in FIG. 10, the first medical device is a catheter 100 having a shaft 102 and the second medical device is an introducer assembly 304.

In another implementation, the first medical device is a first catheter having a first shaft and the second medical device is a second catheter having a second shaft. The first shaft extends through the second shaft. When clamped onto the first shaft, the clamping device can abut the proximal end of the second catheter and prevent further movement of the first catheter relative to the second catheter.

General Considerations

For purposes of this description, certain aspects, advantages, and novel features of the examples of this disclosure are described herein. The disclosed methods, apparatus, and systems should not be construed as being limiting in any way. Instead, the present disclosure is directed toward all novel and nonobvious features and aspects of the various disclosed examples, alone and in various combinations and sub-combinations with one another. The methods, apparatus, and systems are not limited to any specific aspect or feature or combination thereof, nor do the disclosed examples require that any one or more specific advantages be present, or problems be solved.

Although the operations of some of the disclosed examples are described in a particular, sequential order for convenient presentation, it should be understood that this manner of description encompasses rearrangement, unless a particular ordering is required by specific language set forth below. For example, operations described sequentially may in some cases be rearranged or performed concurrently. Moreover, for the sake of simplicity, the attached figures may not show the various ways in which the disclosed methods can be used in conjunction with other methods. Additionally, the description sometimes uses terms like "provide" or "achieve" to describe the disclosed methods. These terms are high-level abstractions of the actual operations that are performed. The actual operations that correspond to these terms may vary depending on the particular implementation and are readily discernible by one of ordinary skill in the art.

All features described herein are independent of one another and, except where structurally impossible, can be used in combination with any other feature described herein.

As used in this application and in the claims, the singular forms "a," "an," and "the" include the plural forms unless the context clearly dictates otherwise. Additionally, the term "includes" means "comprises." Further, the terms "coupled" and "associated" generally mean electrically, electromagnetically, and/or physically (e.g., mechanically or chemically) coupled or linked and does not exclude the presence of intermediate elements between the coupled or associated items absent specific contrary language.

As used herein, the term "proximal" refers to a position, direction, or portion of a device that is closer to the user and further away from the implantation site. As used herein, the term "distal" refers to a position, direction, or portion of a device that is further away from the user and closer to the implantation site. Thus, for example, proximal motion of a device is motion of the device away from the implantation site and toward the user (e.g., out of the patient's body), while distal motion of the device is motion of the device away from the user and toward the implantation site (e.g., into the patient's body). The terms "longitudinal" and "axial" refer to an axis extending in the proximal and distal directions, unless otherwise expressly defined.

In the following description, certain terms may be used such as "up," "down," "upper," "lower," "horizontal," "vertical," "left," "right," and the like. These terms are used, where applicable, to provide some clarity of description when dealing with relative relationships. But these terms are not intended to imply absolute relationships, positions, and/or orientations. For example, with respect to an object, an "upper" surface can become a "lower" surface simply by turning the object over. Nevertheless, it is still the same object.

Unless otherwise indicated, all numbers expressing material quantities, angles, pressures, molecular weights, percentages, temperatures, times, and so forth, as used in the specification or claims are to be understood as being modified by the term "about." Accordingly, unless otherwise indicated, implicitly or explicitly, the numerical parameters set forth are approximations that can depend on the desired properties sought and/or limits of detection under test conditions/methods familiar to those of ordinary skill in the art. When directly and explicitly distinguishing examples from discussed prior art, the example numbers are not approximates unless the word "about" is recited. Furthermore, not all alternatives recited herein are equivalents.

In view of the many possible examples to which the principles of the disclosure may be applied, it should be recognized that the illustrated examples are only preferred examples and should not be taken as limiting the scope of the disclosure. Rather, the scope of the disclosure is at least as broad as the following claims. We therefore claim all that comes within the scope and spirit of these claims.

The invention claimed is:

1. A clamping device for a shaft of a catheter comprising:
a first member comprising an annular element defining a central lumen, the annular element having an outer surface having a non-circular cross-sectional profile;
a second member rotatably coupled to the first member and defining a bore into which the annular element extends, the bore having a non-circular cross-sectional profile;
wherein the clamping device is movable between a first, release state in which the second member is in a first rotational position relative to the first member and the central lumen has a first diameter, and a second, clamped state in which the second member is in a second rotational position relative to the first member and the central lumen has a second diameter, which is less than the first diameter;
wherein when the clamping device is in the clamped state, the clamping device engages an outer surface of a catheter shaft extending through the central lumen and when the clamping device is in the release state, the clamping device can be moved along a length of the catheter shaft; and
wherein when in the clamped state, the bore and the annular element are rotationally offset from one another such that the annular element is compressed by the bore, thereby reducing the diameter of the central lumen.

2. The clamping device of claim 1, further comprising an elastomeric member disposed within the central lumen of the first member, the elastomeric member defining a second lumen sized to receive the catheter shaft.

3. The clamping device of claim 1, wherein the annular element comprises one or more engagement members extending longitudinally along the annular element and defining a non-circular outer profile of the annular element.

4. The clamping device of claim 3, wherein the engagement members comprise chamfered rectangular protrusions.

5. The clamping device of claim 1, wherein when the bore and the annular element are rotationally offset from one another, the engagement members are deflected inwardly toward the central lumen.

6. The clamping device of claim 1, wherein when in the release state, the bore and the annular element are rotationally aligned with one another.

7. The clamping device of claim 1, wherein the bore of the second member comprises a lip portion configured to engage one or more end surfaces of the one or more engagement members such that the first and second members form a snap-fit connection.

8. The clamping device of claim 1, wherein the annular element comprises one or more openings extending longitudinally along the annular element and spaced apart about a circumference of the annular element.

9. The clamping device of claim 8, wherein when the clamping device is in the release state the openings have a first width and when the clamping device is in the clamped state the openings have a second width narrower than the first width.

10. A clamping device for a shaft of a catheter comprising:
a first member comprising an annular element defining a central lumen, the annular element having an outer surface having a non-circular cross-sectional profile;
a second member rotatably coupled to the first member and defining a bore into which the annular element extends, the bore having a non-circular cross-sectional profile;
wherein the clamping device is movable between a first, release state in which the second member is in a first rotational position relative to the first member and the central lumen has a first diameter, and a second, clamped state in which the second member is in a second rotational position relative to the first member and the central lumen has a second diameter, which is less than the first diameter;
wherein when the clamping device is in the clamped state, the clamping device engages an outer surface of a catheter shaft extending through the central lumen and when the clamping device is in the release state, the clamping device can be moved along a length of the catheter shaft; and
wherein the clamping device further comprising a first pair of extension members and a second pair of extension members, wherein when the first pair of extension members abut each other the clamping device is in the release state and when the second pair of extension members abut each other the clamping device is in the clamped state.

11. The clamping device of claim 10, wherein the second pair of extension members comprise indicia configured to indicate to a user that the clamping device is in the clamped state.

12. A clamping device for a shaft of a catheter comprising:
a first member comprising an annular element having a first bore, an outer surface of the annular element having a non-circular shape in cross-section formed by one or more engagement members extending from the outer surface of the annular element;
a second member rotatably coupled to the first member, the second member comprising a body portion including a second bore having a non-circular shape in cross-section into which the annular element extends;
wherein rotation of the first and second members relative to one another moves the clamping device between a first state in which the first bore has a first diameter and a second state wherein the first bore has a second diameter smaller than the first diameter;
wherein when the clamping device is in the second state, the clamping device is configured to engage an outer surface of a catheter shaft extending through the central lumen and when the clamping device is in the release state, the clamping device is configured such that it can move along a length of the catheter shaft; and
wherein when in the release state, the second bore and the annular element are rotationally aligned with one another.

13. The clamping device of claim 12, wherein the first and second members are fixed axially relative to one another.

14. The clamping device of claim 12, wherein when in the second state, the second bore and the annular element are rotationally offset from one another such that the annular element is compressed by the second bore, thereby reducing the diameter of the first bore.

15. The clamping device of claim 14, wherein when the second bore and the annular element are rotationally offset from one another, the engagement members are deflected inwardly toward the central lumen.

\* \* \* \* \*